United States Patent [19]

Wilhelm et al.

[11] 4,045,580
[45] Aug. 30, 1977

[54] PHARMACEUTICAL PREPARATION USING 9-(2-HYDROXY-3-AMINO-PROPYL)-9,10-DIHYDRO-9,10-ETHANO-ANTHRACENES AS ANTIDEPRESSANTS

[75] Inventors: Max Wilhelm, Watchung, N.J.; Raymond Bernasconi, Oberwil, Switzerland; Angelo Storni, Rheinfelden, Switzerland; Dieter Beck, Basel, Switzerland; Karl Schenker, Binningen, Switzerland

[73] Assignee: Ciba-Geigy Corporation, Ardsley, N.Y.

[21] Appl. No.: 659,069

[22] Filed: Feb. 18, 1976

Related U.S. Application Data

[60] Division of Ser. No. 564,580, April 2, 1975, Pat. No. 4,017,542, which is a continuation-in-part of Ser. No. 226,329, Feb. 14, 1972, abandoned.

[30] Foreign Application Priority Data

Feb. 23, 1971 Switzerland .......................... 2578/71
Jan. 17, 1972 Switzerland ............................ 669/72

[51] Int. Cl.$^2$ ........................................... A61K 31/135
[52] U.S. Cl. ................................................... 424/330
[58] Field of Search ..................... 424/330; 260/570.6, 260/501.18, 501.19

[56] References Cited

U.S. PATENT DOCUMENTS

| 2,403,483 | 7/1946 | Cusic ................................. 260/570.8 |
| 2,541,342 | 2/1951 | Cusic ................................. 260/247.7 |
| 3,399,201 | 8/1968 | Schmidt et al. ...................... 260/268 |
| 3,674,841 | 7/1972 | Boissier et al. .................. 260/501.12 |

*Primary Examiner*—Allen J. Robinson
*Attorney, Agent, or Firm*—Joseph G. Kolodny; Theodore O. Groeger; John J. Maitner

[57] ABSTRACT

9-(2-A-3-R-propyl)-9,10-dihydro-9,10-ethano-anthracenes containing the nucleus of the formula

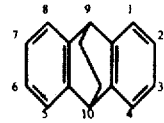

(I)

wherein R denotes a secondary or tertiary amino group and A denotes a free, etherified or acylated hydroxyl group, their pharmaceutically acceptable salts are useful as psychotropics, especially as anti-depressants.

5 Claims, No Drawings

PHARMACEUTICAL PREPARATION USING 9-(2-HYDROXY-3-AMINO-PROPYL)-9,10-DIHYDRO-9,10-ETHANO-ANTHRACENES AS ANTIDEPRESSANTS

This is a division of application Ser. No. 564,580, filed April 2, 1975, Now U.S. Pat. No. 4,017,542 which in turn is a continuation-in-part of application Ser. No. 226,329, filed Feb. 14, 1972, and now abandoned.

SUMMARY OF THE INVENTION

The subject of the invention are 9-(2-A-3-R-propyl)-9,10-dihydro-9,10-ethano-anthracenes containing the nucleus of the formula

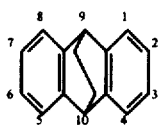

wherein R denotes a secondary or tertiary amino group and A denotes a free, etherified or acylated hydroxyl group, and acid addition salts, particularly pharmaceutically acceptable acid addition salts thereof, as well as process for their manufacture, pharmaceutical preparations containing them and their use as antidepressants.

A N-monosubstituted amino group is described as a secondary amino group and a N-disubstituted amino group is described as a tertiary amino group. Possible substituents are, above all, hydrocarbon radicals of aliphatic character which can also be interrupted by hetero-atoms, such as oxygen, sulphur or nitrogen, and/or be substituted by oxo, hydroxyl and/or amino groups. Hydrocarbon radicals of aliphatic character are radicals of which the first member, bonded to the nitrogen atom, is not a member of an aromatic system. Radicals of this nature are, for example, aliphatic and cycloaliphatic hydrocarbon radicals and especially lower radicals of this nature.

The description lower aliphatic hydrocarbon radicals is used for radicals which contain up to 7, and above all 1–4, carbon atoms. The description lower cycloaliphatic hydrocarbon radicals is used for radicals which possess 3–7, and especially 5 or 6, ring carbon atoms. The word "lower" used in conjunction with other groups containing carbon is to be understood, in the subsequent text, to have the general sense which has just been indicated for hydrocarbon radicals. The hydrocarbon radicals can be saturated or unsaturated.

As radicals of the type indicated, the following should above all be mentioned: lower alkyl and alkenyl radicals, especially radicals with not more than 7 carbon atoms, such as methyl, ethyl, propyl or isopropyl radicals, and butyl, pentyl, hexyl and heptyl radicals which are straight or branched and are bonded at any desired position, lower hydroxyalkyl radicals, such as 2-hydroxyethyl and 3-hydroxypropyl radicals, allyl and methallyl radicals, lower cycloalkyl and cycloalkenyl radicals, such as cyclopentyl, cyclohexyl, cyclopropyl, cyclopentenyl and cyclohexenyl radicals, which are unsubstituted or have one, two or more lower alkyl substituents, lower cycloalkyl-alkyl and cycloalkenyl-alkyl radicals, such as cyclopentyl- and cyclohexenyl-methyl, -ethyl and -propyl radicals which are unsubstituted or have one, two or more lower alkyl substituents.

Divalent radicals are above all lower alkylene and alkenylene radicals which are optionally substituted by hydroxyl, oxo and/or amino groups, especially those radicals which contain 3–7, preferably 4, 5 or 6, chain members and accordingly form rings with 4–8, and preferably 5, 6 or 7, members with the nitrogen atom of the amino groups. Such radicals are, for example, 1,4-butylene, 1,4-pentylene, 1,4-hexylene, 1,5-pentylene, such as 1,5-dimethyl 1,5-pentylene, 3-methyl-1,5-pentylene, 1,5-pentenylene, 1,6-hexylene and 1,5-hexylene radicals. Radicals of this nature which are interrupted by hetero-atoms are above radicals in which the hetero-atom is separated from both ends of the chain by at least two carbon atoms, that is to say the chain contains more than 4, and preferably 5, members and accordingly forms a more than 5-membered, and preferably 6-membered, ring with the nitrogen atom. As examples there may be mentioned:

Lower oxaalkylene, azaalkylene and thiaalkylene radicals which are optionally substituted by hydroxyl, oxo and/or amino groups, such as 3-aza-, 3-oxa-, and 3-thia-1,5-pentylene radicals, such as, for example, 2,4-dimethyl-3-thia-1,5-pentylene, 1,5-dimethyl-3-aza-1,5-pentylene, 3-lower alkyl-3-aza-1,5-pentylene, such as 3-methyl-3-aza-1,5-pentylene, 3-hyxroxy-lower alkyl-3-aza-1,5-pentylene, such as 3-hydroxyethyl-3-aza-1,5-pentylene, 3-oxa-1,6-hexylene and 3-aza-1,6-hexylene radicals.

The amino group is above all a mono- or di-lower alkylamino group, such as the monopropylamino or dipropylamino group, or preferably the monoethylamino or diethylamino group, but above all the dimethylamino group and very particularly the monomethylaminoamino group, or the N-methyl-N-ethylamino group, a cycloalkylamino group, such as the cyclopropylamino, cyclobutylamino, cyclopentylamino or cyclohexylamino group, or a pyrrolidino or piperidino group which is optionally C-lower alkylated and/or β-singly unsaturated in the ring, or an optionally C-lower alkylated piperazino, N'-lower alkylpiperazino, such as N'-methylpiperazino, or N'-(hydroxy-lower alkyl)-piperazino, such as N'-(β-hydroxyethyl)-piperazino, thiomorpholino or morpholino group. The expression "C-lower alkylated" denotes here, as above and in the following text, that the particular radical is substituted at C atoms by lower alkyl radicals, such as those mentioned, and especially by $C_{1-3}$-alkyl radicals.

An etherified hydroxyl group is, for example, a phenyllower alkoxy group, such as benzyloxy group, an alkenyloxy group, above all a lower alkenyloxy group, such as an allyloxy or methallyloxy group, or especially an alkoxy group. Alkoxy groups are, above all, lower alkoxy groups, such as methoxy, ethoxy, propoxy, isopropoxy, butoxy or pentoxy groups.

An acylated hydroxyl group, that is to say an acyloxy group, is preferably derived from a carboxylic acid, for example an aromatic carboxylic acid, such as benzoic acid, or above all from an aliphatic carboxylic acid, such as an alkanoic acid, for example butyric acid, propionic acid and especially acetic acid.

A preferably represents a free hydroxyl group.

The propyl radical which substitutes the 9-position of the anthracene nucleus is preferably only substituted by the radicals A and R, but can be further substituted by lower alkyl radicals, for example those mentioned, above all by methyl of ethyl radicals. The propyl radical mentioned preferably possesses not more than one such alkyl radical as substituent.

In the new compounds, the positions 11 and/or 12 can be substituted by lower alkyl radicals, for example those mentioned, but the positions 11 and 12 are preferably unsubstituted.

The new compounds are preferably unsubstituted inpositions 1-8 of the anthracene ring, but can possess substituents in these positions, for example lower alkyl, alkoxy, alkenyloxy and/or alkylmercapto groups, lower alkylsulphonyl and/or alkanoyl groups, but above all trifluoromethyl or halogen, such as fluorine, bromine and iodine, but very particularly chlorine, alkyl radicals to be mentioned particularly being methyl, ethyl, propyl, isopropyl, butyl, i-butyl and tert. butyl, alkoxy or alkenyloxy groups to be mentioned being the methoxy, ethoxy, allyloxy and methylenedioxy group, alkylmercapto groups to be mentioned being the methylmercapto or ethylmercapto group, and alkanoyl radicals to be mentioned being, above all, the acetyl, propionyl and butyryl radical. There may be several substituents in positions 1-8 but preferably two and above all one. Preferred positions for substituents are the 3-position and very particularly the 2-position.

In the 10-position, the new compounds can possess, for example, an aliphatic hydrocarbon radical, such as one of the abovementioned lower alkyl or alkenyl radicals, or a halogen atom, especially a chlorine atom, but preferably the 10-position is unsubstituted.

In accordance with what has been stated above, the invention relates, for example, to compounds of the formula

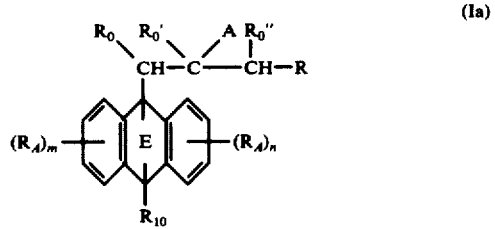

(Ia)

wherein A and R have the abovementioned meanings and A above all denotes a free hydroxyl group, a lower alkoxy group or a lower alkanoyloxy group, $n$ and $m$ each denote an integer from 0 to 4, $n + m$ preferably being not greater than 3, $m$ above all represents 0 and $n$ for example represents 2, but above all 1 and expecially 0, the radicals $R_A$ independently of one another denote the groups mentioned above as substituents of positions 1-8 and a single substituent $R_A$ is preferably in the 3-position or especially in the 2-position, $R_{10}$ denotes one of the groups mentioned above as substituents of the 10-position or especially denotes a hydrogen atom and the symbols $R_o$, $R_o'$ and $R_o''$ represent the lower alkyl radicals, for example those mentioned, such as ethyl groups or above all methyl groups, or above all represent hydrogen atoms, with preferably at most one of the three symbols being different from hydrogen, and E denotes a 1,2-ethylene radical which is optionally substituted in the 1-position and/or 2-position by a lower alkyl radical, for example by one of those mentioned, such as a methyl, ethyl, propyl or isopropyl radical, but is preferably unsubstituted, and acid addition salts, particularly pharmaceutically acceptable acid addition salts thereof.

The new compounds possess valuable pharmacological properties, especially a psychotropic, for example anti-depressant action, as can be demonstrated, for example, in test animals. Thus, they show, for example, an inhibition of the norardrenaline uptake into the heart and brain of rats, when administered in doses of about 0.5 to 10 mg/kg s.c., of about 0.2 to about 5 mg/kg i.v. of about 2 to about 100 mg/kg p.o (Maitre et al., Biochem. Pharmacol., vol. 20, p 2169 (1971)). Furthermore, they act as antagonists of reserpine-induced effects. For example, at doses of about 1 to about 5 mg/kg i.p. or p.o. they antagonize reserpine-induced hypothermia in mice (Askew, Life Sci., vol 10, p. 725 (1963) and Benz and Waser, Ph. D. Thesis, Pharmacol, Inst. of the University of Zurich, Switzerland, 1971) and reserpine-induced palpebral ptosis in rats (Rubin et al., J Pharmacol. Exptl. Therap., vol 120, p. 125 (1957)). Furthermore, at doses of about 0.1 to about 0.5 mg/kg i.p. they show a suppression of the tetrabenazine-induced cataleptic behavior (Wirth et al., Arch. int. Pharmacodyn., vol 115, p. 1 (1958)).

The antidepressant effects of the compounds of the present invention are accompanied by no or only minimal sedative properties at effective antidepressive doses. This can be shown, for example, in mice with the test de la traction, (Courvoisier et al., Psychotropic Drugs, Proc. Int. Symp. Psychotrop. Drugs, Milan, p 373 (Elsevier, Amsterdam, 1957)), in which the novel compounds shown only a negligible inhibition at a dose of about 100 mg/kg s.c. and no effect at a dose of about 200 mg/kg p.o., as well as in mice exhibiting aggression induced by isolation (Valzelli et at., Europ. J. Pharmacol., vol 2, 144 (1967)), in which test a complete inhibition of the aggression with no sedation is shown at a dose of about 30 mg/kg s.c.

The new compounds are, therefore, useful as psychotropic agents, especially as anti-depressants, furthermore as starting materials or intermediates for the manufacture of other valuable compounds, especially pharmaceutically active compounds. Thus, for example, the 9-(3-amino-1-propenyl)-9,10-dihydro-9,10-ethanoanthracenes can be manufactured if, in the new compounds, the group A is eliminated, for example, in the form of water.

Compounds to be singled out are above all those of the formula Ia, wherein R denotes an amino group which has one or two substituents from amongst alkyl radicals, hydroxyalkyl or aminoalkyl radicals, alkenyl radicals, lower cycloalkyl and/or cycloalkenyl radicals which are unsubstituted or have one, two or more lower alkyl substituents, lower cycloalkyl-alkyl and/or cycloalkenyl-alkyl radicals which are unsubstituted or have one, two or more lower alkyl substituents, or denotes a 1-azacycloalkyl or 1-azacycloalkenyl radical which contains 4-8 ring members and can be substituted by hydroxyl, oxo and/or amino groups, or denotes a 1-aza-oxa-cycloalkyl, 1-aza-thia-cycloalkyl or 1-azaazacycloalkyl radical in which the hetero-atoms are separated by at least two carbon atoms and which can be substituted by hydroxyl, oxo and/or amino groups, and A represents a free hydroxyl, lower alkoxy or lower alkanoyloxy group, and acid addition salts, particularly pharmaceutically acceptable acid addition salts thereof.

Particularly valuable compounds are those of the formula Ia wherein R denotes a mono-lower alkylamino or di-lower alkylamino group, a hydroxy-lower alkylamino group, an optionally C-lower alkylated 1-azacycloalkyl group with 5-7 ring members or cycloalkylamino group with 3-7 ring members or an optionally C-lower alkylated morpholino, thiomorpholino, N'-lower-alkyl-piperazino or N'-(hydroxy-lower alkyl)- piperazino group, $R_4$ represents lower alkyl, alkoxy or trifluoromethyl groups or preferably halogen atoms, such as bromine atoms or especially chlorine atoms and $R_{10}$ denotes a halogen atom, preferably a chlorine atom, or above all a hydrogen atom, and A represents a free hydroxyl group or a $C_{1-4}$-alkoxy or $C_{1-4}$-alkanoyloxy group, and acid addition salts, particularly pharmaceutically acceptable acid addition salts thereof.

Compounds to be singled out are above all those of the formula

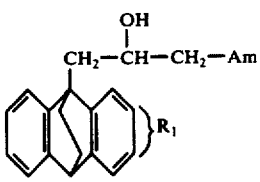

(II)

wherein $R_1$ is preferably in the 2-position and denotes a lower alkyl or alkoxy group, a trifluoromethyl group, a bromine atom or especially a chlorine atom, but above all a hydrogen atom, and Am represents an amino group which is monosubstituted by a $C_{3-7}$-cycloalkyl radical or is monosubstituted or disubstituted by $C_{1-6}$-alkyl groups, or represents an optionally C-lower alkylated pyrrolidino, piperidino, morpholino, N'-methyl-piperazino, N'-ethyl-piperazino or N'-($\beta$-hydroxyethyl)-piperazino group, and acid addition salts, particularly pharmaceutically acceptable acid addition salts thereof.

At the same time, those compounds of the formula II are of particular importance, wherein $R_1$ is in the 2-position and Am denotes a mono- or di-lower alkylamino group, wherein the lower alkyl radicals contain 1–4 carbon atoms, and acid addition salts, particularly pharmaceutically acceptable acid addition salts thereof.

Particularly valuable compounds are those of the formula

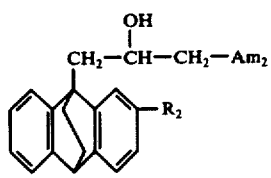

(III)

wherein $R_2$ represents a methoxy group, a trifluoromethyl group but preferably a chlorine atom or above all a hydrogen atom and $Am_2$ denotes the diethylamino group or the monoethylamino group, but above all the dimethylamino group or particularly the monomethylamino group, and acid addition salts, particularly pharmaceutically acceptable acid addition salts thereof, above all the 1-(3-dimethylamino-2-hydroxy-1-propyl)-9,10-dihydro-9,10-ethano-anthracenemethanesulfonate and very particularly the 9-(2-hydroxy-3-methylaminopropyl)-9,10-dihydro-9,10-ethano-anthracene of the formula

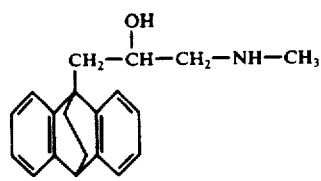

or acid addition salts, particularly pharmaceutically acceptable acid addition salts thereof.

The new compounds are obtained according to methods which are in themselves known.

Thus, for example, a possible procedure is that in a 9-X-9,10-dihydro-9,10-ethano-anthracene, in which X denotes a radical which can be converted into a 2-A-3-R-propyl group, X is converted into a 2-A-3-R-propyl group, R and A having the indicated meanings.

The radical X is, for example, a 2-A-propyl radical which is substituted in the 3-position by a reactively esterified hydroxyl group. A reactively esterified hydroxyl group Z is, above all, a hydroxyl group esterified with a strong organic or inorganic acid, such as, in particular, a hydrogen halide acid, such as hydrochloric acid, hydrobromic acid or hydriodic acid, or with an arylsulphonic acid, such as benzenesulphonic acid which has one, two or more substituents chosen from lower alkyl or alkoxy radicals, for example those mentioned above, or halogen atoms, such as chlorine or bromine atoms, for example p-toluenesulphonic acid or p-bromobenzenesulphonic acid, or with a lower alkanesulphonic acid, for example methanesulphonic acid. Z together with A can also be present as an epoxy bridge.

The conversion of the radical Z into the amino group R is effected, for example, by reaction with an amine of the formula HR, wherein R has the indicated meaning.

The reaction takes place in the customary manner, preferably in the presence of a solvent and optionally in the presence of a condensation agent, for example a basic condensation agent, preferably at elevated temperature and optionally in a closed vessel under pressure. A basic condensation agent is, for example, an alkali hydroxide or alkali carbonate, for example sodium hydroxide or potassium carbonate, or a tertiary amine, for example triethylamine or pyridine. Instead of a secondary amine, an agent which releases such an amine, for example a symmetrically disubstituted urea, can also be used. In this case, the reaction is appropriately carried out with heating, and optionally with addition of an inert diluent, for example diphenyl-ether or sand.

The radical X can furthermore be, for example, a N-unsubstituted 2-A-3-amino-propyl group, which is converted into a N-monosubstituted 2-A-3-amino-propyl group by replacement of a hydrogen atom. The replacement takes place in the usual manner, for example by reaction with a reactive ester of an appropriate alcohol. A reactive ester is above all an ester derived from a strong organic or inorganic acid, such as, in particular, from one of the abovementioned acids, or from sulphuric acid.

$\beta$-Hydroxyalkylamines can also be obtained, for example, by reaction with an optionally appropriately substituted ethylene oxide.

The radical X can also be a radical which can be converted into a 2-A-3-R-propyl group by reduction.

Such a radical is, for example, a radical corresponding to the 2-A-3-R-propyl group which possesses at least one optionally reactively modified oxo group.

The reduction of one or more optionally reactively modified oxo groups to give corresponding compounds with two hydrogen atoms in place of each of the oxo groups, can be carried out in the usual manner. For example, free oxo groups can be reduced with metallic reducing agents, such as zinc and mineral acid, for example hydrochloric acid, or with zinc amalgam and hydrochloric acid, preferably concentrated hydrochloric acid, by the Clemmensen method, to give two hydrogen atoms in each case.

Suitable reactively modified oxo groups are, for example, hydrazono groups, semicarbazono groups or two geminal alkylmercapto groups, such as two geminal methylmercapto or ethylmercapto groups, or ethylene-1,2-dimercapto groups.

Hydrazono or semicarbazono groups can be reduced in the usual manner, for example with alkali alcoholates, such as sodium ethylate, preferably under pressure and at elevated temperature, in accordance with the method of Wolff-Kishner, or by heating a compound containing a hydrazono group with an alkali hydroxide such as sodium hydroxide or potassium hydroxide, in a high-boiling solvent, such as diethylene glycol or triethylene glycol, according to the method of Huang-Minlon or Soffer. Here, the free oxo compounds can also be employed directly instead of the hydrazono compounds and in that case, for example, transiently form hydrazones with hydrazine and alkali hydroxide.

The mercapto groups mentioned can be reduced in the usual manner, for example with Raney nickle and hydrogen in accordance with the thioacetal method, or with zinc amalgam in hydrochloric acid, preferably concentrated hydrochloric acid, to give two hydrogen atoms each.

If oxo groups are adjacent to the nitrogen atom, it being possible for a methyl group substituted by an oxo group to be additionally substituted by an alkoxy group, such as a methoxy or ethoxy group, that is to say if X is, for example, an appropriate 2-hydroxy-2-carbamylethyl group or an appropriate 3-acylamino-2-hydroxypropyl group, such as, for example, also an urethane grouping, or also a cyclic urethane grouping in which X is for example a corresponding 3-amino-2-hydroxypropyl group, wherein the hydroxy- and the amino-group are connected together with a carboxyl group to an oxazolidinon ring, the reduction can be carried out in the usual manner, for example by means of an amide reducing agent, for example a simple or complex hydride, such as borane, for example diborane, or a complex di-light metal hydride, especially an alkali metal-aluminum hydride, such as lithium-aluminum hydride or sodium-aluminum hydride, or an alkoxy-aluminum hydride or -borohydride for example sodium dibutoxyaluminum hydride or sodium trimethoxyborohydride, or an alkaline earth metal-aluminum hydride, such as magnesium-aluminum hydride, or sodium borohydride in a tertiary amine, such as pyridine or triethylamine, or aluminum hydride-aluminum chloride. The reduction can, for example, also be carried out electrolytically on cathodes of high overvoltage, such as mercury, lead amalgam, or lead cathodes. The catholyte used is, for example, a mixture of water, sulphuric acid and a lower alkanecarboxylic acid, such as acetic acid or propionic acid. The anodes can consist of, for example, platinum, carbon or lead, and sulphuric acid is preferably used as the anolyte.

If the oxo group is in the 2-position of the propyl radical, the oxo group is reduced to a hydroxyl group.

The reduction can be carried out in the usual manner, for example with nascent hydrogen, or with a complex metal hydride, for example an alkali borohydride, such as lithium borohydride or sodium borohydride, especially in accordance with the method of Chaikin and Brown, preferably in tetrahydrofurane or ether, for example diethyl-ether, or with an amalgam, such as aluminum amalgam, preferably in an inert neutral solvent, such as ether, for example diethyl-ether.

The reduction can also be carried out in accordance with the method Meerwein-Ponndorf-Verley. Thus, for example, the oxo compound can be treated with a lower alkanol, such as isopropanol, in the presence of a corresponding alcoholate, such as aluminum isopropylate.

If A does not represent a free hydroxyl group, a radical which can be converted by reduction into a 2-A-3-R-propyl group can also be a radical corresponding to the group mentioned, in which the nitrogen is bonded, by one of its substituents, to a double bond and optionally carries a positive charge, and wherein one of the carbon atoms bonded to the nitrogen atom carries a hydroxyl group, such as an appropriate 3-imino- or 3-immonium-2-A-propyl radical, or an appropriate 3-amino- or 3-ammonium-2-A-propyl radical, in which the amino group is doubly bonded to one of the amino substituents.

The conversion is effected in the usual manner by reduction, for example of the azomethine bond. The reduction takes place in the usual manner, preferably by means of a simple or complex hydride, for example a borane, or a di-light metal hydride, for example an alkali metal-earth metal hydride, such as sodium borohydride or lithium aluminum hydride, or an alkoxyaluminum hydride or alkoxyborohydride, or with formic acid. It is however also possible to effect the reduction with hydrogen in the presence of a catalyst, such as a platinum, palladium or nickel catalyst, or of a homogeneous catalyst, for example a complex rhodium compound, such as a rhodium chloro-triphenyl-phosphine complex.

Another radical which can be converted by reduction into a N-monosubstituted 2-A-3-R-propyl group is, for example, also a No-monosubstituted 2-A-3-amino-propyl radical which on the nitrogen atom additionally carries a radical Y which can be slit off by reduction. The conversion is effected by reduction which is carried out in the usual manner.

Y is, for example, an α-aralkyl radical, such as a benzyl radical, or an α-aralkoxycarbonyl radical, such as a carbobenzoyl radical, which can be split off, for example, by hydrogenolysis, for example by reduction with catalytically activated hydrogen, such as hydrogen in the presence of a hydrogenation catalyst, such as a palladium catalyst or a platinum catalyst. Y can however also be a 2-halogeno-alkoxycarbonyl radical, such as, for example, the 2,2,2-trichloroethoxycarbonyl radical or the 2-iodoethoxycarbonyl radical, which can be split off by reduction. For reduction, it is possible to use, above all, reduction with metals (so-called nascent hydrogen), such as, for example, the action of metals or metal alloys, and also of amalgams, preferably in the presence of hydrogen-releasing agents, such as carboxylic acids, alcohols or water. Above all, zinc or zinc alloys in acetic acid are used. Furthermore, chromous compounds, such as chromous chloride or chromous acetate, can also be used. Y can also be an arylsulphonyl group, such as the toluenesulphonyl group, which can be split off in the usual manner, by reduction with nascent hydrogen, for example by means of an alkali metal, such as lithium or sodium, in liquid ammonia. The splitting off of an arylsulphonyl group can also be effected with a hydride, for example one of the abovementioned simple or complex hydrides, preferably lithium aluminum hydride, appropriately in the presence of an inert solvent, such as ether, for example tetrahydrofuran.

A radical X which can be converted by reduction into a 2-hydroxy-3-R-propyl radical is also a 1,2-epoxy-3-R-propyl radical. Radicals of this nature can, in particular, be converted into 2-hydroxy-3-R-propyl radicals by catalytically activated hydrogen, for example by hydrogen in the presence of the abovementioned catalysts.

A radical X which can be converted into a 2-A-3-R-propyl radical is, for example, also a 2-Ya-3-R-propyl radical, wherein Ya denotes a radical which can be converted into a free, etherified or acylated hydroxyl group. Such 2-Ya-3-R-propyl radicals can be converted into a 2-A-3-R-propyl radicals by conversion of Ya into A.

Ya is, for example, a hydrolysable or alcoholisable radical, such as a reactively esterified hydroxyl group, for example one of those mentioned above for Z, which is hydrolysed or alcoholysed in the usual manner, preferably in the presence of basic or acid catalysts, for example alkali hydroxide, such as, for example, sodium hydroxide solution, or sulphuric acid or hydrochloric acid. The alcoholysis is carried out in an appropriate alcohol, preferably using a lower alkanol, such as, for example, ethanol, and at elevated temperature.

If Ya represents a halogen atom, such as a chlorine, bromine or iodine atom, the replacement by a free hydroxyl group can also be effected with moist silver oxide.

Ya can also be an unsubstituted amino group. Such a group Ya can be converted into a hydroxyl group by means of nitrous acid, preferably in a suitable solvent, such as, for example, water, and if appropriate, at an elevated temperature.

X can also represents a 3-R-propenyl radical. Such a radical is converted into a 2-A-3-R-propyl radical by addition of HA, especially of water.

The addition can be carried out in the usual manner, for example in the presence of acid catalysts, above all Lewis acids, for example zinc chloride, aluminum chloride or alumina. The addition can also be carried out according to Brown, for example by hydroboration, that is to say reaction with a borane, for example diborane or a dialkylborane, appropriately in an ether, for example tetrahydrofurane or diethylene glycol dimethyl ether, and in the presence of an acid, for example boron trifluoride or aluminum chloride, and subsequent oxidation, preferably with hydrogen peroxide in the presence of alkali hydroxide, for example sodium hydroxide. The borane can also be formed in situ, for example from sodium borohydride and acid, for example one of the abovementioned acids. The addition can also be effected by oxymercuration, for example by reaction with mercuric salts, such as mercuric chloride or mercuric acetate, in a suitable solvent, for example a tetrahydrofuranewater mixture, and subsequent reduction, for example with sodium borohydride in alkaline solution.

The radical which can be converted into a N-monosubstituted 2-A-3-R-propyl group can also be a radical which can be converted thereto by hydrolysis, such as a N-monosubstituted 2-A-3-amino-propyl radical, which additionally carries on the nitrogen atom a radical Y' which can be split off by hydrolysis, and the radical Y' can additionally also be linked to a hydroxyl group A. The conversion is effected by hydrolytic removal of Y'. The radical Y' is, for example, a silyl radical such as a trimethylsilyl radical, or above all an acyl radical, for example an alkanoyl radical, above all an optionally halogenated, for example fluorinated, lower alkanoyl radical, such as the acetyl radical or trifluoroacetyl radical, a benzoyl radical, phenylalkanoyl radical, carbalkoxy radical, for example the tert, butoxycarbonyl, carboethoxy or carbomethoxy radical, or an arlakoxycarbonyl radical, for example a carbobenzoxy radical. If the radical Y' is additionally also linked to a hydroxyl group A, X represents a (3-substituted-5-oxazolidinyl)-methyl radical which can also be substituted yet further in the 2-position, for example by hydrocarbon radicals of aliphatic character, for example those mentioned above, especially lower alkyl radicals or phenyl-lower alkyl radicals, for example methyl, ethyl, propyl, benzyl, phenethyl or α-methylphenethyl radicals. The radical Y' can however also be a doubly-bonded radical, for example an alkylidene or benzylidene group or a phosphorylidene group, such as a triphenylphosphorylidene group, in which case the nitrogen atom carries a positive charge.

The hydrolytic removal of Y' is effected, for example, by means of hydrolysing agents, for example in the presence of acid agents, such as, for example, dilute mineral acids, such as sulphuric acid or hydrogen halide acids, especially hydrochloric acid, or, in the case of acyl radicals, preferably in the presence of basic agents, for example alkali hydroxides, such as sodium hydroxide.

If Y' is a trifluoroacetyl group, the hydrolysis can also be linked to the introduction of a further substituent, and a tertiary amine thus obtained, if a reactive ester of an appropriate alcohol, for example an ester with the acids mentioned above for this purpose, such as hydriodic acid or methanesulphonic acid, is present in the reaction mixture together with a base, for example potassium hydroxide.

The new compounds can also be obtained if in a 2-A-3-R-propyl-anthracene, wherein R and A have the indicated meanings, a 9,10-ethano radical is introduced.

The introduction of the 9,10-ethano radical is effected in the usual manner. This is appropriately done using optionally lower-alkylated ethylene in accordance with the Diels-Alder method, advantageously in a suitable solvent, such as an aromatic hydrocarbon, for example toluene, and at elevated temperature, and/or under pressure.

In resulting compounds, substituents can be introduced, modified or split off within the framework of the definition of the final substances.

Thus, for example, secondary amines obtained can be converted into tertiary amines, that is to say substituents, for example those mentioned above, can be introduced into N-monosubstituted 2l -A-3-amino-propyl or N' -unsubstituted piperazino groups which are obtained. The introduction is, in particular, effected as indicated above for free 2-A-3-amino-propyl groups.

In resulting compounds which contain free hydroxyl groups, the latter can be etherified. The etherification is carried out in the usual manner, for example by reaction with a reactive ester of an alkanol, preferably in the presence of a strong base.

In resulting compounds which possess etherified hydroxyl radicals, the latter can be converted into free hydroxyl groups in the usual manner. This conversion is effected, for example, by hydrolysis, above all by means of strong acids, such as, for example, hydriodic acid or hydrobromic acid, and if appropriate in the presence of light metal halides, such as aluminum bromide or boron bromide,or by means of pyridine hydrochloride or aluminum chloride in pyridine.

In resulting compounds which contain a free hydroxyl group A, the latter can be acylated. The acylation is carried out in the usual manner, especially by means of reactive, functional derivatives of the acids concerned, preferably acid halides or acid anhydrides, optionally in the presence of acid-binding agents, for example basic agents, such as those mentioned, or, if appropriate, in the presence of acids, for example, those mentioned above. Conversely, it is also possible to split off the acyl radicals in resulting compounds which carry acyloxy groups A. They are split off in the usual manner, for example as indicated above for Y'.

In resulting compounds which contain mercapto groups, the mercapto groups can be oxidised to alkylsulphonyl groups. The oxidation takes place in the usual manner, for example with per-compounds, such as hydrogen peroxide or per-acids, especially organic peracids such as per-acetic acid or a per-benzoic acid.

The invention also relates to those embodiments of the process in which the starting compound is a compound obtainable as an intermediate product at any stage and the missing steps are carried out, or in which the process is stopped at any stage or a starting substance is formed under the reaction conditions or, where appropriate, is used in the form of a salt and/or racemate or optical antipode.

Thus it is also possible, for example, to start from a 9-(2-A-3-oxo-propyl)-9,10-dihydro-9,10-ethano-anthracene and to treat this under reducing conditions with an amine of the formula H-R, or to start from a N-unsubstituted 9-(2-A-3-amino-propyl)-9,10-dihydro-9,10-ethano-anthracene and to treat this under reducing conditions, for example in the presence of formic acid, with an appropriate aldehyde or ketone. In the course thereof, the above mentioned azomethine compounds are introduced as intermediate products. In this case, A should preferably not be present as the free hydroxyl group.

The reactions mentioned are carried out in the usual manner, in the presence or absence of diluents, condensation agents and/or catalysts, at lowered, ordinary or elevated temperature and, if appropriate, in a closed vessel.

Depending on the process conditions and starting substances, the final substances are obtained in the free form or in the form of their acid addition salts, which are also included in the invention. The acid addition salts of the new compounds can be converted into the free compound in a manner which is in itself known, for example by means of basic agents, such as alkalis or ion exchangers. On the other hand, the resulting free bases can form salts with organic or inorganic acids. Acids which are suitable for the formation of therapeutically usable salts are in particular employed for the manufacture of acid addition salts. As examples of such acids there may be mentioned hydrogen halide acids, sulphuric acids, phosphoric acids, nitric acid, perchloric acid, aliphatic, alicyclic, aromatic or heterocyclic carboxylic or sulphonic acids, such as formic, acetic, propionic, succinic, glycollic, lactic, malic, tartaric, citric, ascorbic, maleic, hydroxymaleic or pyruvic acid; phenylacetic, benzoic, p-aminobenzoic, anthranilic, p-hydroxybenzoic, salicyclic or p-aminosalicyclic acid, embonic acid, methanesulphonic, ethanesulphonic, hydroxyethanesulphonic and ethylenesulphonic acid; halogenobenzenesulphonic, toluenesulphonic and naphthalenesulphonic acid or sulphanilic acid; methionine, tryptophane, lysine or arginine.

These or other salts of the new compounds, such as, for example, the picrates, can also be used for the purification of the free bases obtained, by converting the free bases into salts, isolating these and again liberating the bases from the salts. Because of the close relationship between the new compounds in the free form and in the form of their salts, the free compounds are to be understood, in the preceding and following text, where appropriate also to include the corresponding salts, as regards general sense and intended use.

Depending on the choice of the starting substances and procedures, and depending on the number of asymmetrical carbon atoms, the new compounds can be in the form of optical antipodes, racemates or isomer mixtures (for example racemate mixtures).

Resulting isomer mixtures (racemate mixtures) can be separated into the two stereoisomeric (diastereomeric) pure isomers (for example racemates) on the basis of the physicochemical differences of he constituents, in a known manner, for example by chromatography and/or fractional crystallisation.

Resulting racemates can be resolved according to known methods, for example by recrystallisation from an optically active solvent, by means of micro-organisms, or by reaction with an optically active acid which forms salts with the racemic compound and separation of the salts obtained in this manner, for example on the basis of their differing solubilities, into the diastereomers, followed by liberation of the antipodes by the action of suitable agents. Particularly customary optically active acids are, for example, the D- and L-forms of tartaric acid, di-o-toluyltartaric acid, malic acid, mandelic acid, camphorsulphonic acid or quinic acid. Advantageously, the more active of the two antipodes is isolated.

Appropriately, those starting substances are used for carrying out the reactions according to the invention as lead to the final substances which have initially been mentioned by way of examples or been particularly singled out.

Where the starting substances are new they can be obtained according to methods which are in themselves known. New starting substances also form a subject of the invention.

The new compounds can be used, for example, in the form of pharmaceutical preparations in which they are present in the free form or, where appropriate, in the form of their salts, especially the therapeutically usable salts, mixed with a pharmaceutical organic or inorganic, solid or liquid excipient suitable, for example, for enteral or parenteral administraton. Suitable substances for forming the latter are those which do not react with the new compounds, such as, for example, water, gelatine, lactose, starch, stearyl alcohol, magnesium stearate, talc, vegetable oils, benzyl alcohol, gum, propylene glycol, petroleum jelly or other known medicinal excipients. The pharmaceutical preparations can, for example, be in the form of tablets, dragees, capsules or suppositories or in a liquid form, as solutions (for example as an elixir or syrup), suspensions or emulsions. They are optionally sterilised and/or contain auxiliary substances, such as preservatives, stabilisers, wetting agents or emulsifiers, solubilising agents or salts for regulating the osmotic pressure or buffers. They can also contain other therapeutically valuable substances. The pharmaceutical preparations are formulated in accordance with customary methods. Usually, daily doses of about 10 to about 100 mg in the form of pharmaceutical compositions are administered to a host (of about 75 kg) requiring treatment with a compound of the formula I or a pharmaceutically acceptable acid addition salt thereof, particularly with one of the compounds previously mentioned as being preferred.

EXAMPLE 1

3.9 g of 9-[(3-methyl-5-oxazolidinyl)-methyl]-9,10-dihydro-9,10-ethano-anthracene and 60 ml of 2 N hydrochloric acid are warmed to 90° C for 3 hours. Thereafter 5 N sodium hydroxide solution is added until an alkaline reaction is obtained, and the mixture is extracted with methylene chloride. After separation, and evaporation of the solvent, 9-(2-hydroxy-3-methylamino-propyl)-9,10-dihydro-9,10-ethano-anthracene of the formula

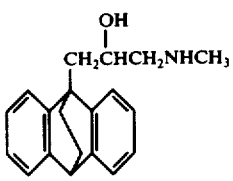

is left. This is dissolved in 10 ml of ethanol, 1 ml of a 10% strength solution of hydrogen chloride in ethanol is added and the mixture is treated with ether. The crystalline hydrochloride of 9-(2-hydroxy-3-methylamino-propyl)-9,10-dihydro-9,10-ethano-anthracene, of melting point 237°–239° C, is thus obtained.

9-[(3-Methyl-5-oxazolidinyl)-methyl]-9,10-dihydro-9,10-ethano-anthracene, required as the starting material, can be manufactured as follows:

10 g of 10% strength palladium on charcoal, poisoned with quinoline-sulphur, are added to a solution of 46 g of 9-(chlorocarbonylmethyl)-9,10-ethano-anthracene in 200 ml of xylene, and hydrogen is then passed through the mixture at 120° C. After 7 hours, the catalyst is filtered off and the filtrate is evaporated in vacuo. The residue is dissolved in methylene chloride and extracted by shaking with sodium carbonate solution. The organic phase is separated off, dried over sodium sulphate and then diluted to a volume of 250 ml by adding methylene chloride. After 1 ml of triethylamine has been added, 20 ml of hydrogen cyanide are added and the mixture is left to stand for 12 hours at room temperature. It is then extracted by shaking with water and the solvent is evaporated. Crystalline 9-(2-hydroxy-2-cyano-ethyl)-9,10-dihydro-9,10-ethano-anthracene is obtained as the residue and after recrystallisation from methylene chloride-petroleum ether has a melting point of 139°–141° C.

This nitrile (18 g) is dissolved in 150 ml tetrahydrofurane and added dropwise to 6 g of lithium aluminum hydride in 100 ml of tetrahydrofurane. After 8 hours' stirring at 60° C, the mixture is cooled, and 8 ml of water, 8 ml of 15% strength sodium hydroxide solution and 24 ml of water are successively added. The precipitate which has separated out is filtered off and the filtrate is evaporated in vacuo. 9-(2-Hydroxy-3-aminopropyl)-9,10-dihydro-9,10-ethano-anthracene of melting point 176°–177° C is left.

20 g of this amino-alcohol in 150 ml of formic acid are warmed with 10 ml of formaldehyde solution to 95° C for 1 hour and the mixture is then evaporated in vacuo. The residue is rendered alkaline by adding 2 N sodium hydroxide solution, the mixture is extracted with methylene chloride and the organic phase is evaporated. 9-[(3-Methyl-5-oxazolidinyl)-methyl]-9,10-dihydro-9,10-ethano-anthracene of melting point 106°–109° C is obtained.

EXAMPLE 2

A solution of 12 g of N-(p-toluenesulphonyl)-9-(2-hydroxy-3-methylamino-propyl)-9,10-dihydro-9,10-ethano-anthracene in 100 ml of tetrahydrofurane is slowly added dropwise to 3 g of lithium aluminium hydride in 50 ml of tetrahydrofurane. Afte the reaction mixture has boiled for 4 hours under reflux, it is cooled to room temperature, and 3 ml of water and 10 ml of 15% strength sodium hydroxide solution are carefully added. The precipitate which has formed is filtered off and the filtrate is evaporated. The residue contains 9-(2-hydroxy-3-methylamino-propyl)-9,10-dihydro-9,10-ethano-anthracene, which is identical to the product obtained in Example 1, and the cyclohexylsulphamate of which has a melting point of 143°–145° C.

The toluenesulphonamide used as the starting material can be manufactured as follows:

25 g of p-toluenesulphonyl chloride are added to a solution of 25 g of 9-(2-hydroxy-3-aminopropyl)-9,10-dihydro-9,10-ethano-anthracene in 200 ml of pyridine. After 12 hours, water is added, and after adding 50 ml of 5 N hydrochloric acid, the mixture is extracted with methylene chloride. The crystalline residue which is left after drying and evaporating the solvent is dissolved in 150 ml of dimethylformamide and treated with a solution of diazomethane in ether. After standing for 12 hours at room temperature, the solution is evaporated in vacuo. Crude N-(p-toluenesulphonyl)-9,10-dihydro-9,10-ethano-anthracene is obtained as the residue and can be used without further purification for the reaction described above.

EXAMPLE 3

5 Grams of 9-(2-p-tosyloxy-3-dimethylamino-propyl)-9,10-dihydro-9,10-ethano-anthracene and 2 g of sodium hydroxide are boiled under reflux for 2 hours in 50 ml of ethanol and 5 ml of water. There are then added 100 ml of water and 50 ml of 2N acetic acid and the mixture is extracted with ether. The aqueous phase is isolated and made alkaline by addition of 10% sodium hydroxide solution. After extraction with methylene chloride and evaporation of the solvent, the 9-(2-hydroxy-3-dimethylamino-Propyl)-9,10-dihydro-9,10-ethano-anthracene of the formula

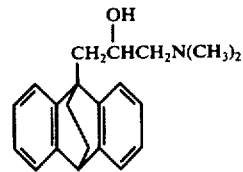

remains as residue in the form of a crystalline substance which melts at 118°–121° C after sublimation. The methane sulphonate melts at 185°–186° C.

EXAMPLE 4

A mixture of 10 g of 9-(2-hydroxy-3-aminopropyl)-9,10-dihydro-9,10-ethano-anthracene, 10 ml of a 35% solution of formaldehyde in water and 100 ml of formic acid is heated for 1 hour to 100° C. The mixture is then evaporated to dryness in vacuo and the residue dissolved in 100 ml of 2N acetic acid. After washing with ether, the acid solution is treated with 10% sodium hydroxide solution until it shows alkaline reaction and the liberated base is then extracted with methylene chloride. The methylene chloride extract is dried and the solvent evaporated to yield as residue 9-(2-hydroxy-2-dimethylaminopropyl)-9,10-dihydro-9,10-ethanoanthracene, which after sublimation melts at 118°-121° C and is identical with the product obtained in Example 3. The methane sulphonate melts at 185°-186° C.

EXAMPLE 5

To a solution of 1.0 g of lithium-aluminium-hydride in 20 ml of tetrahydrofuran is added a solution of 2.1 g of 5-[9,10-dihydro-9,10-ethano-9-anthrylmethyl]-oxazolidin-(2)-one in 20 ml of tetrahydrofuran. The mixture is boiled under reflux for 4 hours, subsequently cooled, and then there are added 2 ml of water, 2 ml of 15% sodium hydroxide solution, and a further 6 ml of water. The precipitate which has formed is filtered off, the filtrate is evaporated and the residue is taken up in acetic acid after evaporation of the solvent. The acid solution is extracted with ether, made alkaline with 10% sodium hydroxide soltution and the base extracted with methylene chloride. The solvent is evaporated to yield as residue the 9-(2-hydroxy-3-methylamino-propyl)-9,10-ethano-anthracene whose hydrochloride melts at 237°-239° c and which is identical with the product described in Example 1.

The oxazolidone used as starting material can be manufactured as follows:

To a solution of 2.8 g of 9-(2:hydroxy-3-aminopropyl)-9,10-dihydro-9,10-ethano-anthracene in 50 ml of benzene, 20 ml of dioxan and 5 ml of 2N sodium hydroxide are added dropwise and with stirring at room temperature 20 ml of a 10% solution of phosgene in toluene. The precipitated portion is filtered off after 3 hours and the filtrate is evaporated. The residue is dissolved in methylene chloride and the methylene chloride solution is extracted with a 3% aqueous solution of methanesulphonic acid. The extract is dried and the solvent evaporated to yield as residue the crude 5-[9,10-ethano-9-anthryl-methyl]-oxazolidin-(2)-one in the form of a solid substance.

EXAMPLE 6

18 Grams of 9-(2,3-epoxy-propyl)-9,10-dihydro-9,10-ethano-anthracene and 20 g of methylamine are heated in 150 ml of ethanol for 4 hours at 90° C and the mixture is subsequently evaporated in vacuo. The residue is dissolved in ether and the ether solution extracted with 2N acetic acid. The acid solution is then made alkaline with 10% sodium hydroxide solution and the base extracted with ether. The ethereal extract is dried and the ether evaporated to yield as residue 9-(2-hydroxy-3-methylaminopropyl)-9,10-dihydro-9,10-ethano-anthracene whose hydrochloride melts at 237°-239° C and which is identical with the product obtained in Example 1.

The epoxide used as starting material can be manufactured as follows:

To a solution of 46 g of 9-(chlorocarbonylmethyl)-9,10-dihydro-9,10-ethano-anthracene in 200 ml of xylene are added 10 g of 10% palladium carbon which is contaminated with quinoline-sulphur. Then at 120° C hydrogen is passed in and after 7 hours the catalyst is filtered off and the reaction mixture evaporated on vacuo. The residue is dissolved in methylene chloride and the methylene chloride solution is extracted with sodium carbonate solution. The organic phase is isolated, dried and evaporated, to yield as residue the crude 9,10-dihydro-9,10-ethano-anthryl-acetaldehyde.

To convert the aldehyde into the epoxide, 19.6 g of trimethyloxosulphonium iodide are added to 2.2 g of sodium hydride in 175 ml of dimethyl sulphoxide. When evolution of hydrogen has ceased, a solution of 21 g of the crude 9,10-dihydro-9,10-ethano-9-anthryl-acetaldehyde in 35 ml of dimethyl sulphoxide is added dropwise and the batch is stirred for 20 minutes at room temperature and then for 30 minutes at 55°-60° C. The reaction mixture is then poured into 300 ml of water and after extraction with methylene chloride, the methylene chloride solution is isolated and evaporated to yield as residue the crude 9-(2,3-epoxy-propyl)-9,10-dihydro-9,10-ethano-anthracene in the form of a viscous oil.

EXAMPLE 7

7.0 Grams of methyl iodide are added to a solution of 5.6 g of 9-(2-hydroxy-3-amino-propyl)-9,10-dihydro-9,10-etnano-antracene in 50 ml of ethanol and the mixture is heated to 60° C. The reaction mixture is subsequently evaporated in vacuo and the residue is dissolved in ether. The ether solution is extracted with 2N acetic acid. The acid solution is made alkaline with 10% sodium hydroxide solution and after extraction with methylene chloride and evaporation of the solvent, there remains as residue an oil which is dissolved in 5 ml of ethanol. To this solution are added 1.5 g of methanesulphonic acid and upon addition of ether, crystallization commences. Repeated recrystallization from ethanol/ether yields the methane sulphonate of 9-(2-hydroxy-3-dimethylamino-propyl)-9,10-dihydro-9,10-ethano-anthracene (m.p. 185°-186° C) which is identical with the product obtained in Example 3.

EXAMPLE 8

The following compounds, for example, can also be manufactured analogously to the procedure described in Examples 1-7, or according to another of the processes described above: 9-(2-hydroxy-3-cyclopropylamino-propyl)-9,10-dihydro-9,10-ethano-anthracene, 9-[2-hydroxy-3-(N'-methylpiperazino)-propyl]-9,10-dihydro-9,10-ethano-anthracene, 9-[2-hydroxy-3-(β-hydroxyethylamino)-propyl]-9,10-dihydro-9,10-ethano-anthracene, 9-{2-hydroxy-3-[N'-(β-hydroxyethyl)-piperazino]-propyl}-9,10-dihydro-9,10-ethano-anthracene, 2-chloro-9-(2-hydroxy-3-cyclopropylamino-propyl)-9,10-dihydro-9,10-ethano-anthracene, 2-chloro-9-[2-hydroxy-3-(N'-methylpiperazino)-propyl]-9,10-dihydro-9,10-ethano-anthracene, 2-chloro-9-[2-hydroxy-3-(β-hydroxyethylamino)-propyl]-9,10-dihydro-9,10-ethano-anthracene and 2-chloro-9-{2-hydroxy-3-[N'-(β-hydroxyethyl)-piperazino]-propyl}-9,10-dihydro-9,10-ethano-anthracene.

EXAMPLE 9

In an analogous fashion, the following compounds can be prepared:

9-(2-hydroxy-3-isopropylamino-propyl)-9,10-dihydro-9,10-ethano-anthracene, 2-chloro-9-(2-hydroxy-3-isopropylaminopropyl)-9,10-dihydro-9,10-ethano-anthracene, 9-(2-methoxy-3-methylamino-propyl)-9,10-dihydro-9,10-ethano-anthracene and 2-chloro-9-(2-methoxy-3-methylamino-propyl)-9,10-dihydro-9,10-ethano-anthracene.

EXAMPLE 10

Tablets containing 25 mg of 9-(2-hydroxy-3-methylamino-propyl)-9,10-dihydro-9,10-ethano-anthracene hydrochloride may be prepared as follows:

| Ingredients (for 10000 Tablets): | |
|---|---|
| 9-(2-hydroxy-3-methylamino-propyl)-9,10-dihydro-9,10-ethano-anthracene hydrochloride | 250 g |
| lactose | 340 g |
| wheat starch | 300 g |
| colloidal silicic acid | 50 g |
| talc | 50 g |
| magnesium stearate | 10 g |
| water | q.s. |

METHOD

The active substance is mixed with the lactose, part of the wheat starch, and with colloidal silicic acid, and the mixture passed through a sieve. Another portion of the wheat starch is pasted with the five-fold quantity of water on a water bath, and the powder mixture is kneaded with the paste until a slightly plastic mass is obtained. The mass is forced through a sieve, dried, and the dry granulate is again passed through a sieve. Then the remainder of the wheat starch, talc and magnesium stearate are admixed. The resulting mixture is compressed into tablets of 100 mg each.

EXAMPLE 11

A mixture of 14 g of the diastereomeric mixture of 2-chloro-9-(2,3-epoxy-propyl)-9,10-dihydro-9,10-ethano-anthracene in 50 ml of benzene and of 50 ml of a 33% solution of methylamine in absolute ethanol is stirred for 84 hours at room temperature in a closed vessel. The reaction mixture is evaporated at about 11 mm Hg and the residue is dissolved in 50 ml of ethanol. The solution is treated with 4 ml of a 10% solution of hydrogen chloride in ethanol and diluted with diethyl ether. The hydrochloride of the diasteromeric mixture of the 2-chloro-9-(2-hydroxy-3-methylamino-propyl)-9,10-dihydro-9,10-ethano-anthracene, which melts at 218°-220° after being recrystallized twice from a mixture of ethanol and diethyl ether, is thus obtained.

In an analogous manner 3 g of the diastereomeric mixture of 2-chloro-9-(2,3-epoxy-propyl)-9,10-dihydro-9,10-ethano-anthracene is reacted with 10 ml of a 33% solution of dimethylamine in ethanol and one obtains the diasteromeric mixture of 2-chloro-9-(3-dimethylamino-2-hydroxy-propyl)-9,10-ethano-anthracene; the compound is reacted with cyclohexane sulfamic acid and the salt resulting after recrystallization from a mixture of ethanol and diethyl ether melts at 168°-169°.

The starting material is prepared in the same manner as the starting material used in Example 6 by reducing the 2-chloro-9-cyanomethyl-9,10-dihydro-9,10-ethano-anthracene with diisobutyl-aluminiumhydride in toluene, followed by acidic hydrolysis and reacting the resulting (2-chloro-9,10-dihydro-9,10-dihydro-9-anthryl)-acetaldehyde with dimethyloxosulfonium methylide (resulting from the treatment of trimethyloxosulfonium iodide with sodium hydride) in dimethyl sulfoxide.

EXAMPLE 12

Tablets containing 10 mg of 9-(2-hydroxy-3-methylaminopropyl)-9,10-dihydro-9,10-ethano-anthracene-hydrochloride are prepared as follows:

| Ingredients (for 50000 tablets): | |
|---|---|
| 9-(2-hydroxy-3-methylamino-propyl)-9,10-dihydro-9,10-ethano-anthracene-hydrochloride | 500.00 g |
| lactose | 2250.00 g |
| corn starch | 1250.00 g |
| tricalcium phosphate | 500.00 g |
| silicagel (in aerogel form) | 250.00 g |
| talc | 100.00 g |
| magnesium stearate | 75.00 g |
| stearic acid | 75.00 g |
| water | q.s. |

A mixture of the 9-(2-hydroxy-3-methylamino-propyl)-9,10-dihydro-9,10-ethano-anthracene-hydrochloride, the lactose and the tricalcium phosphate is moistened with a paste prepared from the corn starch and water, and the silicagel is kneaded into the moist mixture. The still moist mass is granulated, the granulate is dried and then milled. The talc, the magnesium stearate and the stearic acid are added to the powder and the mixture is compressed into tablets of 100 gm weight. Tablets containing 25 mg of the 9-(2-hydroxy-3-methylamino-propyl)-9,10-dihydro-9,10-ethano-anthracene-hydrochloride are prepared according to the above procedure by using 1250.00 g of the pharmacologically active compound and 1500 g of the lactose.

We claim:

1. An antidepressant pharmaceutical preparation comprising an antidepressively effective amount of a member selected from the group consisting of a compound of the formula

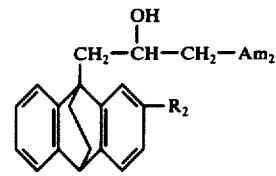

wherein $R_2$ represents a member selected from the group consisting of trifluoromethyl, chloro and hydrogen, and $Am_2$ denotes a member selected from the group consisting of diethylamino, monoethylamino, dimethylamino and monomethylamino, and a pharmaceutically acceptable acid addition salt thereof, together with a pharmaceutical carrier.

2. The preparation as claimed in claim 1, wherein the effective compound is a member selected from the group consisting of 9-(2-hydroxy-3-methylamino-propyl)-9,10-dihydro-9,10-ethano-anthracene and a pharmaceutically acceptable acid addition salt thereof.

3. The preparation as claimed in claim 1, wherein the effective compound is a member selected from the group consisting of 9-(2-hydroxy-3-dimethylamino-propyl)-9,10-dihydro-9,10-ethano-anthracene and a pharmaceutically acceptable acid addition salt thereof.

4. The preparation as claimed in claim 1, wherein the effective compound is a member selected from the group consisting of 2-chloro-9-(2-hydroxy-3-methylamino-propyl)-9,10-dihydro-9,10-ethano-anthracene and a pharmaceutically acceptable acid addition salt thereof.

5. The preparation as claimed in claim 1, wherein the effective compound is a member selected from the group consisting of 2-chloro-9-(2-hydroxy-3-dimethylamino-propyl)-9,10-dihydro-9,10-ethano-anthracene and a pharmaceutically acceptable acid addition salt thereof.

* * * * *